United States Patent
Brunner et al.

(10) Patent No.: US 10,548,484 B2
(45) Date of Patent: Feb. 4, 2020

(54) SENSOR DEVICE FOR ELECTRICAL IMPEDANCE TOMOGRAPHY IMAGING, ELECTRICAL IMPEDANCE TOMOGRAPHY IMAGING INSTRUMENT AND ELECTRICAL IMPEDANCE TOMOGRAPHY METHOD

(75) Inventors: Josef X. Brunner, Chur (CH); Pascal Olivier Gaggero, Bienne (CH); Nicolas Robitaille, St. Augustin-de-Desmaures (CA)

(73) Assignee: Swisstom AG, Landquart (CH)

( * ) Notice: Subject to any disclaimer, the term of this patent is extended or adjusted under 35 U.S.C. 154(b) by 1306 days.

(21) Appl. No.: 13/878,401

(22) PCT Filed: Oct. 4, 2011

(86) PCT No.: PCT/CH2011/000236
§ 371 (c)(1),
(2), (4) Date: Apr. 8, 2013

(87) PCT Pub. No.: WO2012/045188
PCT Pub. Date: Apr. 12, 2012

(65) Prior Publication Data
US 2013/0190577 A1 Jul. 25, 2013

(30) Foreign Application Priority Data
Oct. 7, 2010 (CH) .................... 1638/10

(51) Int. Cl.
*A61B 5/0205* (2006.01)
*A61B 5/00* (2006.01)
(Continued)

(52) U.S. Cl.
CPC ........ *A61B 5/0205* (2013.01); *A61B 5/04085* (2013.01); *A61B 5/1135* (2013.01); *A61B 5/6831* (2013.01); *A61B 7/003* (2013.01)

(58) Field of Classification Search
CPC ......... A61B 5/00; A61B 7/00; A61B 5/04085; A61B 5/0205; A61B 5/1135;
(Continued)

(56) References Cited

U.S. PATENT DOCUMENTS

2004/0006279 A1* 1/2004 Arad (Abboud) ... A61B 5/0536
600/506
2004/0034307 A1 2/2004 Johnson et al.
(Continued)

FOREIGN PATENT DOCUMENTS

DE 10301202 B3 1/2004
WO 2000033733 A1 6/2000
(Continued)

OTHER PUBLICATIONS

Hahn, G., et al. "Local mechanics of the lung tissue determined by functional EIT." Physiological measurement 17.4A (1996): A159.*
(Continued)

*Primary Examiner* — Luther Behringer
*Assistant Examiner* — Sean D Mattson
(74) *Attorney, Agent, or Firm* — Morriss O'Bryant Compagni Cannon, PLLC

(57) ABSTRACT

A sensor device for EIT imaging comprises an electrode array for measuring an impedance distribution, with at least one sensor for determining spatial orientation of the electrode array coupled to the electrode array. An EIT imaging instrument is connectable to a sensor for determining spatial orientation of a test person, and optionally in addition connectable to a sensor for gathering information on electrical and/or acoustic activity and/or a sensor for gathering information on dilation. A computing device is connected or integrated for adjusting impedance data based on spatial data, which spatial data describe the spatial orientation of a test subject. An EIT imaging method for measuring an
(Continued)

impedance distribution and adjusting said measured impedance distribution comprises measuring impedance distribution by using an impedance distribution measuring device comprising an electrode array, and transforming the measured impedance distribution into EIT images.

18 Claims, 9 Drawing Sheets

(51) Int. Cl.
*A61B 5/0408* (2006.01)
*A61B 5/113* (2006.01)
*A61B 7/00* (2006.01)

(58) Field of Classification Search
CPC ....... A61B 5/0536; A61B 5/6802; A61B 5/08; A61B 5/061; A61B 5/6831; A61B 7/003
See application file for complete search history.

(56) References Cited

U.S. PATENT DOCUMENTS

| | | | |
|---|---|---|---|
| 2004/0236202 A1 | 11/2004 | Burton | |
| 2004/0260167 A1* | 12/2004 | Leonhardt | A61B 5/0536 600/390 |
| 2005/0107833 A1 | 5/2005 | Freeman et al. | |
| 2006/0293609 A1* | 12/2006 | Stahmann | A61B 5/0537 600/547 |
| 2009/0084674 A1* | 4/2009 | Holzhacker | A61B 5/0536 204/286.1 |
| 2009/0131759 A1* | 5/2009 | Sims | A61B 5/1135 600/301 |
| 2010/0168589 A1* | 7/2010 | Banet | A61B 5/02125 600/490 |
| 2010/0198101 A1* | 8/2010 | Song | A61B 5/0536 600/547 |
| 2010/0228143 A1* | 9/2010 | Teschner | A61B 5/0536 600/547 |
| 2010/0298899 A1* | 11/2010 | Donnelly | A61B 5/02055 607/6 |

FOREIGN PATENT DOCUMENTS

| | | |
|---|---|---|
| WO | 2005094369 A2 | 10/2005 |
| WO | 2006109072 A2 | 10/2006 |
| WO | 2006121469 A1 | 11/2006 |
| WO | 2009035965 A1 | 3/2009 |
| WO | 2009042637 A2 | 4/2009 |

OTHER PUBLICATIONS

Alder, A. and Guardo, R, Electrical impedance tomography: regularized imaging and contrast detection, IEEE Trans Med Imaging, 1996,15 170-179.

Brunner et al, "Imaging of local lung ventilation under different gravitational conditions with electrical impedance tomography" Acta Astronautica, Jan. 31, 2007, pp. 281-284, vol. 60, 4-7, Pergamon Press, Elmsford, GB.

Costa et al, "Electrical impedance tomography" Current Opinion in Critical Care, Feb. 2009, pp. 18-24, vol. 15 (1), Lippincott Williams & Wilkins, United States.

Frerichs et al, "Gravity-dependent phenomena in lung ventilation determined by functional EIT" Physiological Measurement, Nov. 1, 1996, pp. A149-A157, vol. 17, No. 4A, Institute of Physics Publishing, Bristol, GB.

Hedenstierna et al, "Pulmonary densities during anaesthesia. An experimental study on lung morphology and gas exchange" European Respiratory Journal, Jun. 1989, vol. 2, issue 6, p. 528-535.

\* cited by examiner (a)  (b)

SENSOR DEVICE FOR ELECTRICAL IMPEDANCE TOMOGRAPHY IMAGING, ELECTRICAL IMPEDANCE TOMOGRAPHY IMAGING INSTRUMENT AND ELECTRICAL IMPEDANCE TOMOGRAPHY METHOD

CROSS-REFERENCE TO RELATED APPLICATIONS

This application is a national phase entry under 35 U.S.C. § 371 of PCT/CH2011/000236 filed Oct. 4, 2011, which claims priority to Swiss Patent Application No. 1638/10 filed Oct. 7, 2010, the entirety of each of which is incorporated by this reference.

TECHNICAL FIELD OF THE INVENTION

This invention relates to a sensor device for electrical impedance tomography imaging (EIT imaging) comprising an electrode array for measuring an impedance distribution, an EIT imaging instrument connectable to a sensor device comprising an electrode array, an EIT imaging method for measuring an impedance distribution and adjusting said measured impedance distribution.

BACKGROUND OF THE INVENTION

Electrical impedance tomography (EIT) is a non-invasive imaging technique used to investigate and measure regional lung ventilation and perfusion (flow of blood) in humans and animals. In contrast to conventional methods, EIT does not require the patient to breathe through a tube or sensor, does not apply ionizing X-rays and can be used for extended periods, say 24 hours or even longer. EIT can be used continuously and is therefore suited for monitoring treatment effects in real time and over time. EIT was first used to monitor respiratory function in 1983 and remains the only bedside method that allows continuous, non-invasive measurements of regional changes in lung volume, blood flow, and cardiac activity. More details of this technique can be found in "Electrical impedance tomography" by Costa E. L., Lima R. G., and Amato M. B. in Curr Opin Crit Care, February 2009, 15(1), p. 18-24.

In EIT, as disclosed by U.S. Pat. No. 5,626,146, a plurality of electrodes, typically 8 to 32, are arranged on the surface of the body to be examined. A control unit ensures that an electrical signal, for example a current is applied to one or several pairs of electrodes on the skin to establish an electrical field which in turn is measured by the other electrodes. The electrodes used to apply current are called "current injecting electrodes" although one of them might serve as reference ground. Typically, 3 to 10 mA RMS are injected at a frequency ranging from 0.1 to 10000 kHz. With the remaining electrodes, the resulting voltages are measured (forming the "EIT data vector" or the "scan frame") and subsequently used to estimate the distribution of electric impedance within the body. Specific algorithms were developed to convert the set of voltages into images. These conversions are subject to two major challenges: the first is that the mathematical problem is ill-posed and non-linear, the second is inaccuracies of the measured voltages due to variations in amplifiers and current sources.

To overcome the ill-posed nature of impedance estimation, most EIT imaging algorithms make use of additional assumptions, restrictions or constrains. Typical methods known in the art are the use of a-priori knowledge about the internal structure of the medium and regularization to select a particular solution. Examples of a-priori knowledge include anatomical structures, functions of organs, physical characteristics of tissue like conductivity, blood flow, timing of heart contraction, and the like.

In the case of respiratory monitoring, a-priori knowledge can be derived, for example, from flow or volume measurements at the airway opening or from an X-ray image of the chest or from a CT scan, giving the contour and major structures of a patient's chest. Regularization methods enable to algorithmically decide between competing solutions, producing an image that is a reasonable estimation of the true impedance distribution within the thorax. Anatomical and physiological knowledge as well as physical laws form the basis for regularization methods which are known in the art. For example, abrupt changes in intra-thoracic impedance distribution are usually discarded as non-physiological. Gravity influences the distribution of blood pool and blood flow and therefore the distribution of impedance. Depending on the posture, the disease of the patient and the intra-thoracic location of the impedance distribution, gravity has significant effects on the measured signals. It is known that mechanically ventilated intensive care patients in supine position suffer from regional lung collapse in the dorsal regions of the lungs. Such collapse can lead to or aggravate acute lung injury. Postural change, for example turning the patient to the side or on his front (prone position) may reverse the collapse and can thus have beneficial therapeutic effects.

A three-zone-model may be used to demonstrate the influence of gravity (Hedenstierna G. et al. Pulmonary densities during anaesthesia. An experimental study on lung morphology and gas exchange. Eur Respir J. 1989 June; 2(6):528.) The three zones of this model are:

Zone 1: open and well aerated alveoli;
Zone 2: unstable alveoli in which their opening and closing occurs during the respiratory cycle;
Zone 3: collapsed alveoli.

These zones develop for example as a result of patients lying on their back (supine position) or on their stomach (prone position). In healthy subjects, the zones usually disappear in the upright position. The degree or level of zone expression within the lungs may vary with respect to the gravity vector. But the degree or level of zone expression usually remains unchanged on a horizontal plane orthogonal to the gravity vector. Ventilation-induced lung injury due to the cyclic opening and closing of lung units is assumed to happen mainly in zone 2. Hypoxemia is caused by the shunting of blood through the non-aerated zone 3. It is a treatment goal to eliminate those two zones in patients.

In mechanically ventilated patients, oxygenation can be improved by changing the body position of the patient. The mechanism behind such improvement is that collapsed lung spaces, described as Zone 3 above, are being opened in the new body position and thus oxygenation of blood is improved. Rotating the body of a mechanically ventilated patient into defined lateral positions to improve lung function is known in the art as disclosed in international application WO2005/094369.

Based on above knowledge, it might seem quite obvious to use EIT to monitor the operation of the lung to detect dysfunctions such as a collapse of the lung and the reversal of this collapse. However, in practice collapsed areas are difficult if not impossible to see on EIT images.

To overcome inaccuracies of measured voltages in the electrical impedance tomography method, it is known to use time-difference images, i.e. images that are calculated with reference to an image taken at a particular previous point in time. Such time-difference images are generated from changes in impedance relative to a baseline or reference condition. This relative or differential approach cancels out systematic measurement errors as well as some errors related to incorrect assumptions about thoracic shapes, body composition and contact impedance, since the same errors are assumed to be present in all images in a proportional way. Plotted rapidly in sequence, like a movie, these images create a representation of gas and blood flow in and out of each lung region and allow the care giver to evaluate lung function in real time. Thus, the dynamics of organ functions such as the beating of the heart and the breathing of the lungs can be monitored. Pre-requisite for stable time-difference images are a sound reference image. For this purpose, the sum or average of all values of a scan frame (composite EIT signal or plethysmogram) is often used. It is assumed, that the onset of a breath (start of inspiration) corresponds to a local minimum of the composite EIT signal and the reference image is therefore taken exactly at this point. However, in patients with small tidal volumes and low signal-to-noise ratio, for example in intensive care patients, the composite EIT signal is weak and exact determination of the onset of inhalation is nearly impossible. With the EIT instrumentation available at the present, artefacts create false signals very easily, introduce errors and bias, and ultimately lead to erroneous clinical decisions.

Document WO 2006/121469 A1 describes an EEG system comprising a cap with electrodes and motion sensors. The electrodes record the EEG signals. The motion sensors acquire motion data, which may include noise signals associated with the patient movement, blood flow motion and ballistocardiac motion within the patient. The data are processed to reduce motion noise from the EEG signals.

Some recently published EIT methods are the following:

WO 00/33733 A1 refers to a method for the regional determination of the alveolar opening and closing of the lung depending on the respiration pressure, wherein with the method of electrical impedance tomography an impedance signal is measured in at least one lung zone depending on the respiration pressure.

Document WO 2009/035965 A1 discloses an instrument and a method for assessing regional oxygen uptake by a patient. For achieving this, two electrical impedance tomography images measured at different times are compared. One image is taken shortly after inhaling the second image is taken after holding the breath for some time. Regional differences in lung volume are interpreted to correlate with oxygen consumption.

Document US 2004/034307 A1 is concerned with reflection tomography imaging using wave field energy such as ultrasound. This method is performed on a body which is immersed in a liquid filled container. Sensors and receivers are positioned at a distance from the body.

In the scientific paper by Brunner et al., titled "Imaging of local lung ventilation under different gravitational conditions with electrical impedance tomography", in ACTA Astronautica, Pergamon Press, Elmsford, G B, Bol. 60 No. 4-7 (2007), it is referred to EIT imaging of lung ventilation under different gravitational conditions. Regional lung ventilation depends on the amount and direction of applied gravitational force. The gravitational influence varies with the position and orientation of a test person. The paper describes how parameters, which are attributed to four regions of interest, change depending on the tilting angle of a test person.

Above scientific paper demonstrates the influence of gravity on lung perfusion and lung ventilation. The existence of regional differences is known in the art and methods to expose these differences are disclosed by the cited publications and others. However, none of the hitherto disclosed methods allows for compensation of gravitational influences and artefacts.

A need for improved EIT instrumentation and analysis methods exists, which allow to monitor lung function and direct therapy. In particular long term EIT observation is expected to improve diagnosis and subsequent treatment. For example, due to continuous EIT monitoring, regional lung ventilation and regional lung collapse could be evaluated, the potential for lung injury assessed, and life saving treatment options, for example lung recruitment manoeuvres, initiated. Especially intensive care patients could greatly profit from an improved electrical impedance tomography technology and continuous monitoring by EIT.

Therefore, it is an advantage of the present invention to provide a device and a method that is able to measure and compute reliable EIT difference images. It is another advantage to provide a device and method that allows one to monitor lung function accurately and in real time. Furthermore, it is an advantage to create improved reference images and to improve utility and usability of EIT technology. Moreover, it is an advantage to improve regularization methods.

SUMMARY OF THE INVENTION

Above advantages are achieved by providing and using spatial information in order to create improved EIT images. Spatial information comprises data describing body position and/or orientation, i.e. the spatial orientation of the body or a body part. For example standard regularization methods are extended by integrating spatial information, i.e. information about orientation and position of a body part, such as e.g. the thorax, during EIT analysis.

In detail, above advantages are achieved with an inventive sensor device, an inventive EIT imaging instrument and an EIT imaging method.

The inventive sensor device for EIT imaging, comprising an electrode array for measuring an impedance distribution, is characterized in that at least one sensor for gathering spatial information (i.e. for determining spatial orientation of a test person) is coupled to the electrode array. The spatial information comprises information about the orientation and/or position of the sensor. The sensor may for example be affixed at the electrode array itself or may be positioned in a defined relation with respect to the electrode array and therefore with respect to a body part which is tested. Consequently, the spatial information comprises information about the orientation and/or position of a test subject (test person), notably the body part tested. Advantageously in practice said spatial information describes the spatial orientation and/or position of the electrode array, which is affixed to a test subject. Data of the position and/or orientation of the sensor can be transformed into data defining the orientation of the body part tested with respect to the gravitational vector, i.e. with respect to the direction of the gravity vector. Thus, e.g. when impedance of the thorax (or another body part) is measured, the spatial information gathered describes the orientation of the thorax, and thus of the lungs (or said other body part), with regard to the gravitational force. Spatial information about orientation and position of a test person, in particular of an electrical impedance tested body part, is prerequisite for adjusting impedance distribution measurement data with regard to gravitational influences. At least one sensor for determining spatial orientation of a test subject may be coupled to the electrode array. Hereby, for example, the spatial orientation of the test subject is determined in relation to the direction of the gravity vector.

The additional spatial information described is highly useful to create clinically usable images and movies. A device that is able to provide reliable EIT difference images depending on body position has not been described previously.

Advantageously the at least one sensor for determining spatial orientation of a test person comprises a spatial data sensor, such as a three-dimensional acceleration sensor, which is also called tri-axial acceleration sensor or gravity sensor. This sensor is used to determine the position or orientation, advantageously, with respect to the gravity vector. A simple acceleration sensor, such as e.g. a monoaxial acceleration sensor, which is able to detect movements only, but which is not able to measure position or orientation, does not suffice for the mentioned purpose.

Conveniently the electrode array forms an array of electrodes which define an observation area within an observation plane.

Advantageously the electrodes of the electrode array are arranged in and/or on a belt-like structure. This allows quick and easy handling of the electrodes and easy positioning and fitting of the electrodes onto body parts. When the sensor for determining spatial orientation of a test person is integrated into or fixed to said belt-like structure, handling, positioning and fitting of the sensor device becomes particularly easy. The electrode array, in particular the belt-like structure, may be elastic, e.g. comprises elastic components. The elastic array or belt-like structure is stretchable at least in its longitudinal extension. The feature of elasticity of the array or belt-like structure allows a tight fitting of the electrode array on the body and at the same time the movement of body parts, such as e.g. the respiratory movement of the chest, is not constrained by the array or belt-like structure. During respiration the elastic array or belt-like structure dilates and shortens in length rhythmically.

Advantageously at least one sensor for gathering information on electrical activity is coupled to the electrode array. Electrical activity is most notably induced by the movements of the heart, i.e. by activity of the heart. Thus, this sensor allows to collect information relating to the activity of the heart.

Conveniently the at least one sensor for gathering information on electrical activity comprises an electro-cardiography sensor, which may be connectable to an electrocardiograph.

Advantageously at least one sensor for gathering information on acoustic activity is coupled to the electrode array. Acoustic activity is most notably induced by the contraction of the heart and the opening and closing of its valves, i.e. by activity of the heart. Thus, this sensor allows to collect information relating to the activity of the heart.

Conveniently the at least one sensor for gathering information on acoustic activity comprises a microphone or phonocardiography sensor, which may be connectable to a phonocardiograph.

Advantageously at least one sensor for gathering information on changes in the circumference or the dilation of the electrode array during inspiration is integrated in or attached to the electrode array. This sensor allows to collect data relating to the breathing activity of a test person.

Conveniently the at least one sensor for gathering information on dilation comprises a strain gauge. The sensor for gathering information on dilation may detect the dilation of a body part, in particular of the chest, during respiration. When using an array of electrodes in or on a belt-like structure, said sensor may detect changes of the circumference of a body part. Advantageously a strain gauge integrated or attached to the belt-like structure is used to collect data on the dilation of the belt-like structure and, therefore, on the changes of the circumference of a body part.

The inventive EIT imaging instrument is connectable to a sensor for determining spatial orientation of a test person and, optionally, in addition the inventive EIT imaging instrument is connectable to a sensor for gathering information on electrical and/or acoustic activity and/or a sensor for gathering information on dilation. According to the invention said EIT imaging instrument is characterized in that a computing device is connected thereto or integrated therein for the purpose of adjusting impedance data based on spatial data (i.e. spatial orientation data) and optionally in addition based on dilation data and/or electrical and/or activity data. The spatial data advantageously describe the spatial orientation of a test subject (e.g. by detecting the orientation of the sensor for determining spatial orientation of a test person, more particularly by detecting the orientation of the electrode array coupled to said sensor). Advantageously the mentioned spatial data describe spatial orientation in respect of the direction of the gravity vector. The computing device comprises a program routine for analyzing said spatial data and adjusting the impedance data. Advantageously the computing device correlates the spatial data with simultaneously (i.e. near-simultaneously) measured impedance data. The computing device uses microprocessor and memory generally available and usually already comprised in a standard EIT imaging instrument. An EIT imaging instrument with integrated functionality to measure and analyze spatial information is more versatile than state of the art EIT imaging instruments. Furthermore, due to the integration of the new functionality, the inventive EIT imaging instrument will be easy to operate.

The inventive EIT imaging method for measuring an impedance distribution and adjusting the measured impedance distribution comprises the steps of (i) measuring impedance distribution by using an impedance distribution measuring device comprising an electrode array and (ii) transforming the measured impedance distribution into EIT images. According to the invention said EIT imaging method is characterized in that values of the measured impedance distribution are adjusted, e.g. enhanced and/or modified, for gravitational influences. In more detail said EIT imaging method is characterized in that the spatial orientation of a test subject is determined (notably by measuring the spatial orientation of the electrode array) and in that values of the measured impedance distribution are adjusted based on said spatial orientation in order to account for gravitational influences. Adjustment according to gravitational influences may be effected in that values of the measured impedance distribution are enhanced and/or modified for gravitational influences. The described adjustment for gravitational influences allows to create visually enhanced and thus clinically more meaningful images and movies. The spatial orientation of the electrode array is linked to orientation and/or position of a tested body part. Advantageously the electrode array is in contact with the skin of a test subject and may be affixed on a body part to be tested.

Advantageously such visualization of gravitational influences is based on a determination of the spatial orientation of the impedance distribution measuring device, in particular the spatial orientation of the electrode array. Since the electrode array is attached to the body of a test person, the orientation of the electrode array is linked to or rather depends on the position of the test person and in particular to the position of the body part tested. By detecting the orientation of the impedance distribution measuring device, in particular of the electrode array, during the measurement of the impedance distribution, adjustment according to gravitational influences becomes possible. The spatial information, for example based on body position and orientation, allows to compute clinically usable images and movies. The new method permits near-real time computation and enables immediate diagnosis and life saving treatment if necessary.

A gravity vector is may be used to describe the spatial orientation of the electrode array and therefore of the test person. Thus, the spatial orientation of the test subject or the electrode array is measured with respect to the direction of the gravity vector.

The spatial orientation of a test subject, in particular e.g. the gravity vector, is may be measured during the measurement of the impedance distribution.

The spatial orientation of a test subject, in particular e.g. the gravity vector, is may alternatively be measured near-simultaneously with the impedance distribution.

Advantageously, values of the impedance distribution and of the spatial orientation of a test subject, in particular e.g. values of the gravity vector, are measured within 1 second, within 500 milliseconds, within 100 milliseconds, or within 10 milliseconds. For a successful adjustment, the delay between the measurement of the spatial information on orientation, e.g. the gravity vector, and the measurement of the impedance distribution should not be more than a few milliseconds.

Advantageously, the impedance distribution measuring device comprises at least an electrode array; the electrode array may be arranged in a belt-like structure.

Advantageously, the measured impedance distribution is additionally synchronized with the electrical activity of the heart.

Information on electrical activity may be measured using an electrocardiography sensor.

Advantageously, the measured impedance distribution is additionally synchronized with the acoustic activity of the heart.

Information on acoustic activity may be measured using a microphone or a phonocardiography sensor.

Advantageously, the measured impedance distribution is additionally adjusted according to changes in the circumference or dilation of an observation area, i.e. of the observed body part, whereby the observation area is e.g. defined by the electrode array. More specifically, the position of the electrode array on a body part defines an observation area.

Information on changes in circumference or dilation may be measured using a strain gauge. The strain gauge is e.g. arranged on the impedance distribution measuring device, i.e. on a belt-like electrode array. The detected changes in the circumference or dilation of the impedance distribution measuring device when arranged around a body part (e.g. the chest of a test person) allows to document temporal changes in the circumference of the chest due to breathing activity. Information on chest movement may alternatively be measured using an acceleration sensor. For measuring movement e.g. a simple mono-axial acceleration sensor is sufficient. However, if e.g. a tri-axial acceleration sensor is used, data relating to movement and orientation may be detected with the same sensor.

BRIEF DESCRIPTION OF THE DRAWINGS

The invention is hereinafter described with reference to the figures.

DETAILED DESCRIPTION OF THE INVENTION

Figure 1:
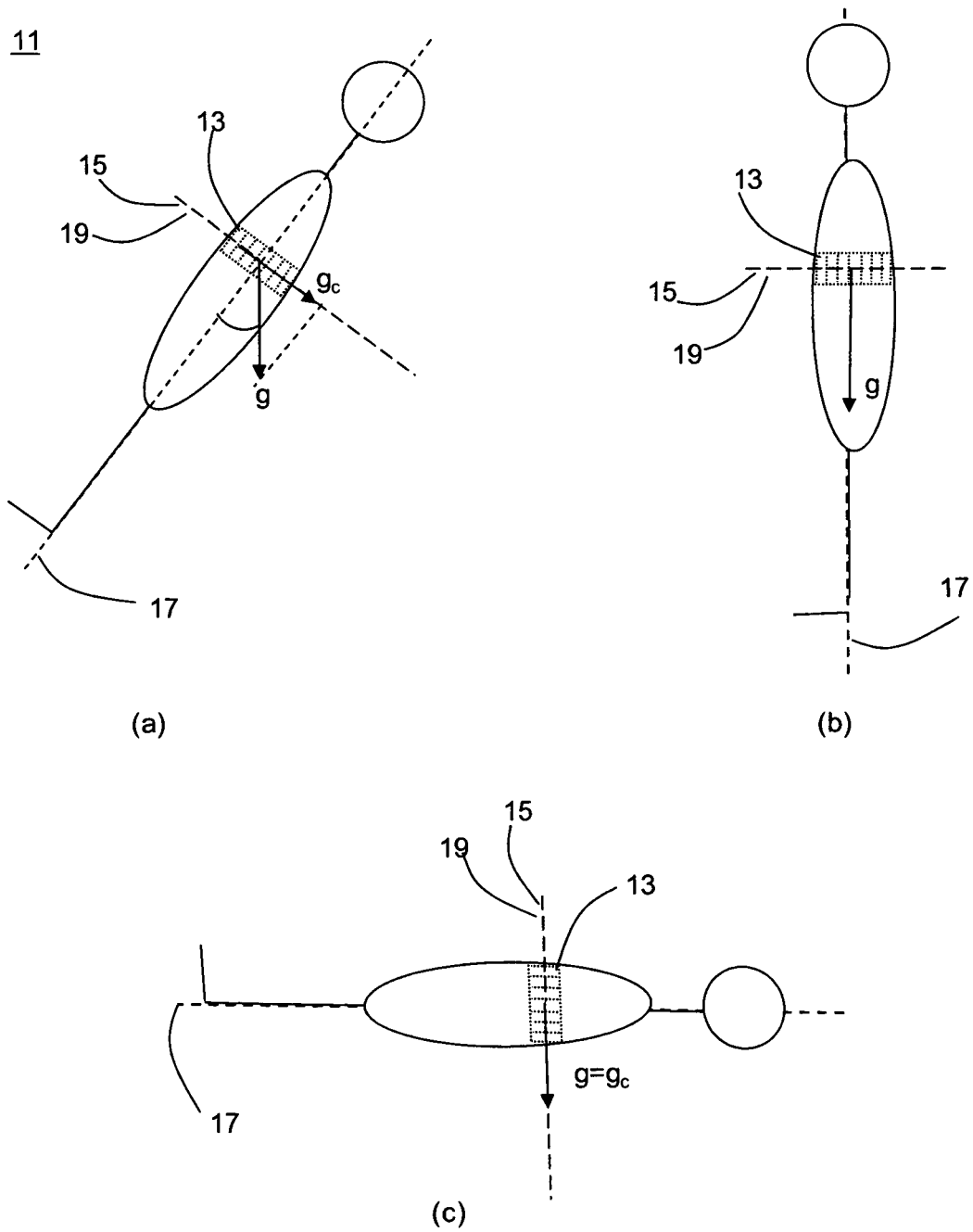
FIG. 1 is a test person in random spatial position.

While this invention is susceptible of embodiments in many different forms, certain embodiments of the invention are shown in the drawings and will herein be described in detail, with the understanding that the present disclosure is to be considered as an exemplification of the principles of the invention and is not intended to limit the broad aspects of the invention to the embodiments illustrated.

As known in the art, EIT data is obtained by a plurality of electrodes that are placed around the chest of a test person 11, e.g. as depicted in FIG. 1. In the present invention, the electrodes may be mounted on a belt-like structure 13 which holds them in a geometrically defined position relative to a body part of a test person 11. In practice an observation plane 15 may be selected by placing a belt-like structure 13 assembled with an array of multiple electrodes around a body part. The exact arrangement of electrodes is not important for the present invention. An arrangement as shown in FIG. 1 is such that the positions of the electrodes define an observation plane 15 (also called electrode plane), for example around the circumference of the chest of a test person 11. In this arrangement the observation plane 15, as e.g. defined by the EIT belt 13, is perpendicular to the main cranio-caudal body axis 17 (anteroposterior axis or saggital axis of the trunk). Angle α (alpha) is defined by the position of the body axis with respect to the gravity vector g. Thus, a is the angle between the main body axis 17 and the gravity vector g. The vector g can be decomposed into two components with one of these components ($g_c$) lying in a plane that is perpendicular to the body axis, for example the observation plane defined by the EIT belt, as shown in FIG. 1.

A first pair of electrodes is used, as known in the art, to inject current or apply a voltage (excitation signals) to establish an electrical field. The voltages or currents resulting from the application of the excitation signal are subsequently measured at each remaining electrode. The excitation signal is then moved to a next pair of electrodes and the measuring sequence is repeated. In an arrangement of 32 electrodes, for example, 32×32 measurements result per measurement loop. The measurements of each loop are sometimes called "scan frame" or "EIT data vector".

According to present invention, spatial information on the orientation of a test person is gathered in addition to information about said established electrical field. For example a three-dimensional acceleration sensor (for example a Bosch BMA150 sensor Integrated Circuit) is mechanically coupled with the belt in order to enable the measurement of spatial information and electrical field information simultaneously. The acceleration sensor measures the gravity vector. Implicitly, the angle (i.e. angle $\alpha$ in FIG. 1) between the gravity vector g and the electrode plane 15 is measured since acceleration sensor and belt are mechanically coupled. The regularization, for example by means of a spatial filter F (see example below), is thereafter optimized to give weight to solutions that show homogeneity in the horizontal plane perpendicular to the gravity vector component $g_c$. The weight, herein referred to as k, is also a function of the angle $\alpha$ of the gravity vector relative to the observation plane and user-defined factors c and d which determine the desired contrast. In one embodiment, the relationship between k and $\alpha$ is a sine function.

Figure 2:
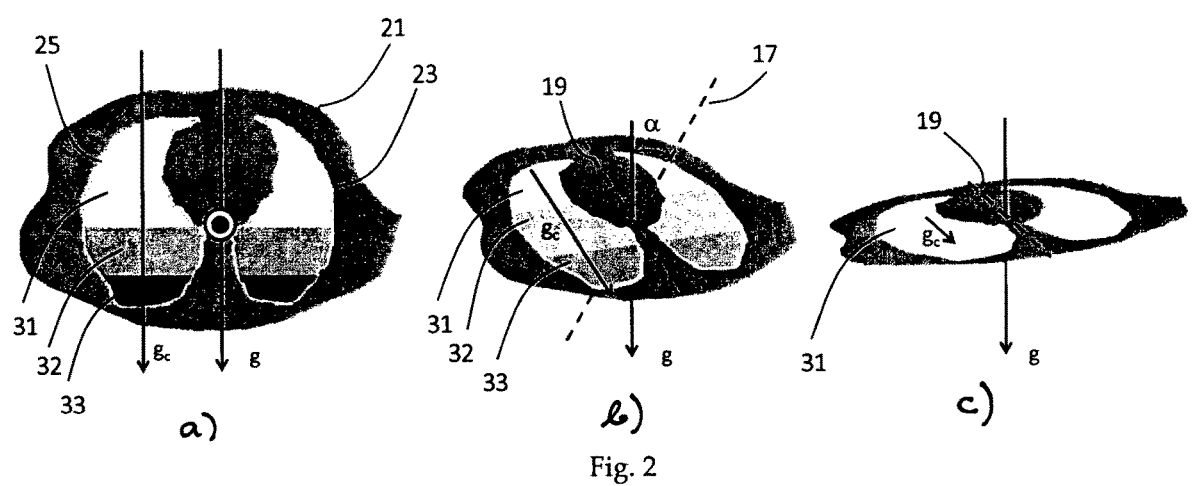
FIG. 2 is a thoracic cut of a test person in three different orientations with respect to the gravity vector, (a) supine position, (b) back leaning position, (c) upright position, and position-dependent zone distribution.

Thus the relationship between the angle $\alpha$, the weight k and the factors c and d can be expressed by the following equation. Hereby $\alpha$ is the angle between the body axis and the gravitation vector g (the definition of $\alpha$ is depicted in FIGS. 1 and 2):

$$k=c^*\gamma(\alpha)+d,$$

where $\gamma$ could be a linear function of $\alpha$ or a sine function of $\alpha$ to allow for smooth transitions.

The acceleration sensor is mechanically connected to the belt-like structure 13 which contains the electrodes. It measures the orientation of the sensor belt relative to the gravity vector g, such as an angle $\alpha$ in space in degrees or radians.

In FIG. 2, thoracic cuts are shown in different orientations with respect to the gravity vector g. Within the thorax 21, the two lungs 23 and 25 are located on the right and left sides. For illustration, where applicable the zones of a 3-zone model (as introduced above) are shown in three different shades in each lung. According to the model the zones extend usually in layers that are perpendicular to the gravitational vector. The first zone 31 is marked in light gray, the second zone 32 in gray, and the third zone 33 in dark gray. According to the model the aeration of the alveoli is reduced in zone 2 and further reduced or even absent in zone 3 due to collapse of alveoli. If the gravitational vector is within (i.e. parallel to) the observation plane, then the zones 1, 2 and 3 are maximally expressed (FIG. 2a). In other words, the three zones are clearly distinguishable if the gravitational vector g is perpendicular to the main body axis 17. FIG. 2a shows this situation by means of the supine position, where the main body axis (shown as black dot in white circle) is perpendicular to the drawing plane. If the body is inclined, the gravitational vector moves outside the observation plane and the zones become much less pronounced (FIG. 2b). In the upright position (FIG. 2c), the angle $\alpha$ is about zero and the zones disappear almost completely. From FIGS. 2a to 2c, the zone expression becomes weaker as the observation plane is inclined further relative to the gravitational vector.

If the gravitational vector g is within the observation plane 15, then the zones of a three-zone model are maximally expressed, as shown in FIG. 2a. The zones remain also expressed—although to a lesser extent—for any body positioning, where the gravitational vector g is outside the observation plane, i.e. where $\alpha$ is different from 90 degrees (FIGS. 2a and 2b), because there is always a component $g_c$ of the gravitational vector g within the observation plane, except when a equals zero ($\alpha$=0). With decreasing angle $\alpha$, starting from 90 degrees, the zones become less pronounced and disappear completely at about 0 degree (FIG. 2c). Typically, this relationship is expressed as a sine function. However, other functions may be used instead.

In upright patients (FIG. 2c), the gravitational vector follows the body axis of a person and zones 1 to 3 follow from the tip of the lungs (apex) to the diaphragm. In this position, the zones 1 to 3 will not manifest themselves on the cross-sectional EIT image. If the patient is in supine position, zone 3 is located on the back (dependent region) while zone 1 is located towards the chest (independent region). In supine position (FIG. 2a), the zones 1 to 3 are within the plane of observation and thus impact the EIT images. If a patient is positioned in the prone position, the zones 1 to 3 are still in the plane of observation but in reversed order.

Above depicted body positions include all positions from supine to upright position. However, positions where the body is turned or twisted sideways are not considered yet. Turned body positions may be described by the dorsoventral axis 19 penetrating the plane defined by the main body axis 17 and the gravity vector g. The dorsoventral axis 19 is defined to be perpendicular to the main body axis 17 (as illustrated in FIG. 1). Turned positions may be relevant or important even when doing short examinations, since the patient may be advised to take a certain position during the EIT measurement. Therefore, a maximum of possible positions should be accounted for, including but not limited to sideways turned positions.

Figure 3:
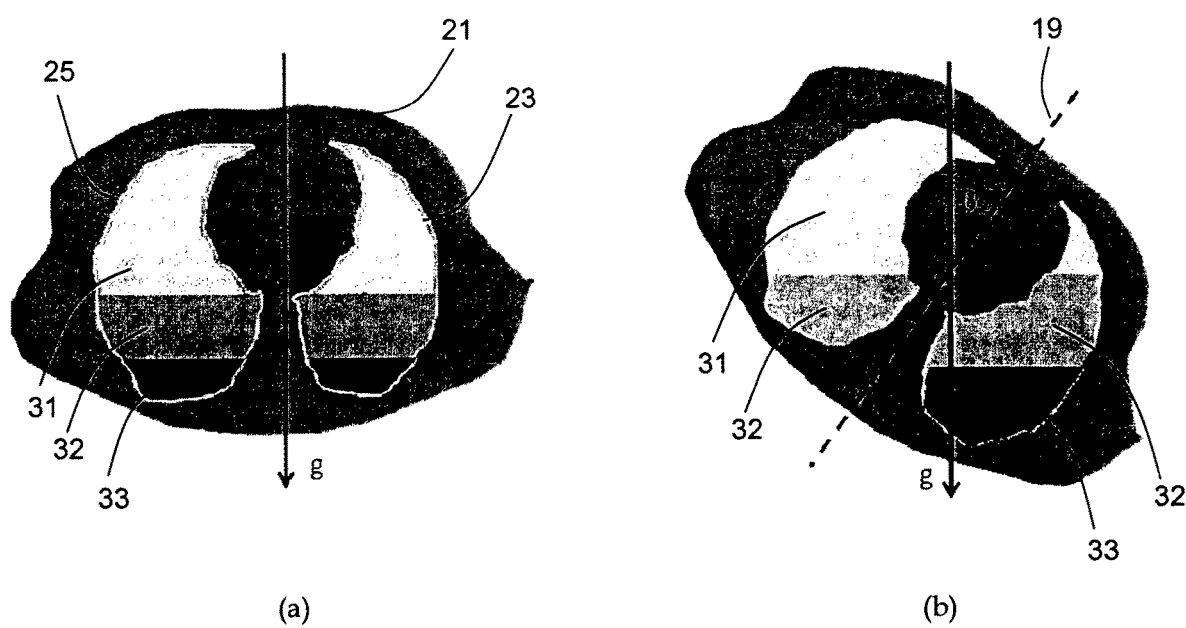
FIG. 3 is a thoracic cut of a test person in two different positions with respect to the gravity vector, (a) full supine position, (b) laterally turned supine position, and position-dependent zone distribution.

In FIGS. 3a and 3b is shown the zone distribution of a thorax in varied lying positions. In said Figures, the zone distribution of a thorax in neutral supine position (FIG. 3a) is compared with the zone distribution of a thorax in sideways turned supine position (FIG. 3b). In sideways turned supine position, according to FIG. 3b, angle $\beta$ is defined by the position of the dorsoventral axis 19 with respect to the gravity vector g. As depicted above and in FIG. 1c, in lying position gravity vector g equals to gravity vector component $g_c$. Thus in general, in lying position, e.g. in supine or in sideways turned supine position, $\beta$ is the angle between the dorsoventral saggital axis and the gravity vector component $g_c$. Also when the test person takes a position between supine position and upright position and is additionally turned to one side, $\beta$ is the angle between the dorsoventral axis 19 and the gravity vector component $g_c$. The dependency of the zone formation on the rotation around the longitudinal axis 17 of the patient is reflected in an asymmetry of the zone distribution in the two lungs. The zones are stacked in layers that are perpendicular to the gravitational vector g. If the body is turned to one side by the angle $\beta$, the zones still follow gravity as shown in FIG. 3b. In this example, the angle $\alpha$ of the gravity vector g relative to the body axis remains unchanged at 90 degrees. In other words, the gravitational vector lies within the observation plane and the zones are maximally expressed. In the sideways turned position, the mechanically ventilated lung situated lower (i.e. the right lung in FIG. 3b) may experience extensive aeration reduction, while the other lung (i.e. left lung) is affected barely.

Figure 4:
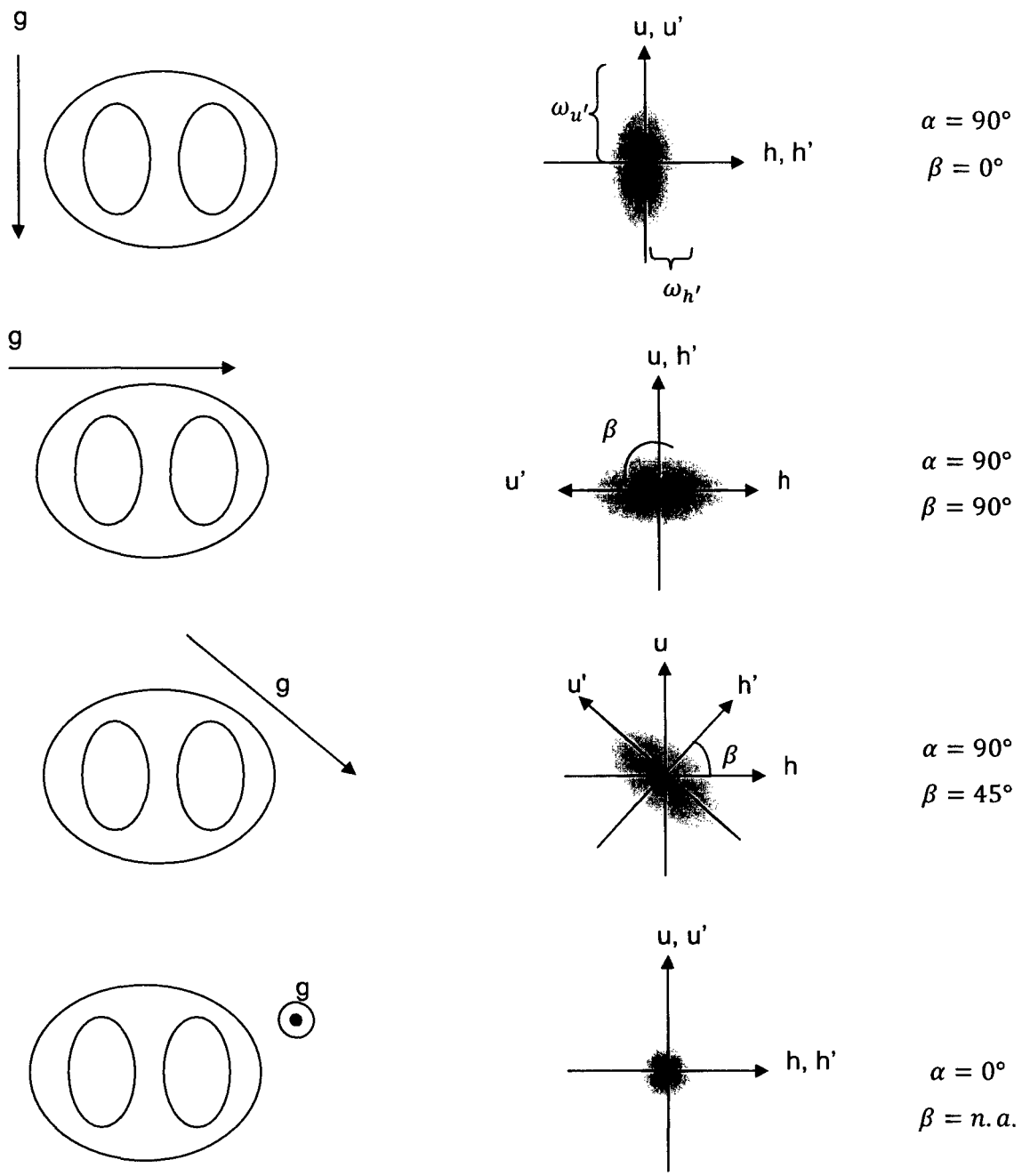
FIG. 4 is a definition of u-h axis system and u'-h' axis system based on the spatial orientation of the observation plane with respect to the gravity vector. Examples of filters are shown on the right-hand side of the picture.

In FIG. 4, left side, various positions of the patient (schematic of the thorax) are depicted with respect to the gravitational vector g. On the right side are shown respective angles α and β by which the two coordinate systems u/h and u'/h' are related to each other. Both coordinate systems have the same point of origin. Again, α represents the angle between the main body axis 17 and the gravity vector g, and β, represents the angle between the dorsoventral axis 19 and the gravity vector component $g_c$. In the orientations given in the first three positions of FIG. 4, gravitational vector component $g_c$ equals gravitational vector ($g_c$=g) and angle β defines the rotation angle between the u/h axis system and the u'/h' axis system. In the bottom example (upright position), angle β is not defined ($g_c$=0), but it does not matter since there is hardly any zone expression. Vectors $w_u'$ and $w_h'$ result from the respective rotation of the u'/h' axis system versus the u/h axis system and define a rotated variant of the spatial filtering (see below).

In further embodiments the invention combines spatial sensor data (which may be measured with a tri-axial acceleration sensor, for determining the orientation) and temporal sensor data (which are for example measured with a dilation sensor, a further acceleration sensor and/or an electrical and/or acoustic activity sensor) to improve the images and related information obtained by EIT.

In one embodiment, the excursion (i.e. dilation or expansion) of the belt-like structure, or parts of the belt-like structure is measured, for example by a strain gauge. A signal processor calculates the deviation from a local minimum and subsequently projects the onset of inhalation back in time. The data vector that was measured at that back-projected point in time is taken as the "breath reference vector". Since this procedure involves a certain delay in image processing, the goal of implementation is to find the balance between accuracy and timing. Since breathing in adults is done at frequencies well above three breaths per minute and well below 50 breaths per minute, a delay of a few hundred milliseconds can be tolerated and should be sufficient to reliably generate the reference point in time. In fact, pulmonary function testing often relies on a test called "occlusion test" to measure the respiratory drive of a patient. Such a test is done in 100 milliseconds in adults and in children. Finally, the "breath reference vector" is subtracted from each EIT data vector, making visible impedance changes that are caused by breathing activities and ventilation.

In one embodiment, the dilation sensor (also called breath sensor) is measuring the force on the belt-like structure by means of a strain-gauge and the body position by means of a 3D acceleration sensor. The user may input two parameters c and d to adjust the image with respect to zones 1, 2, and 3.

Figure 5:
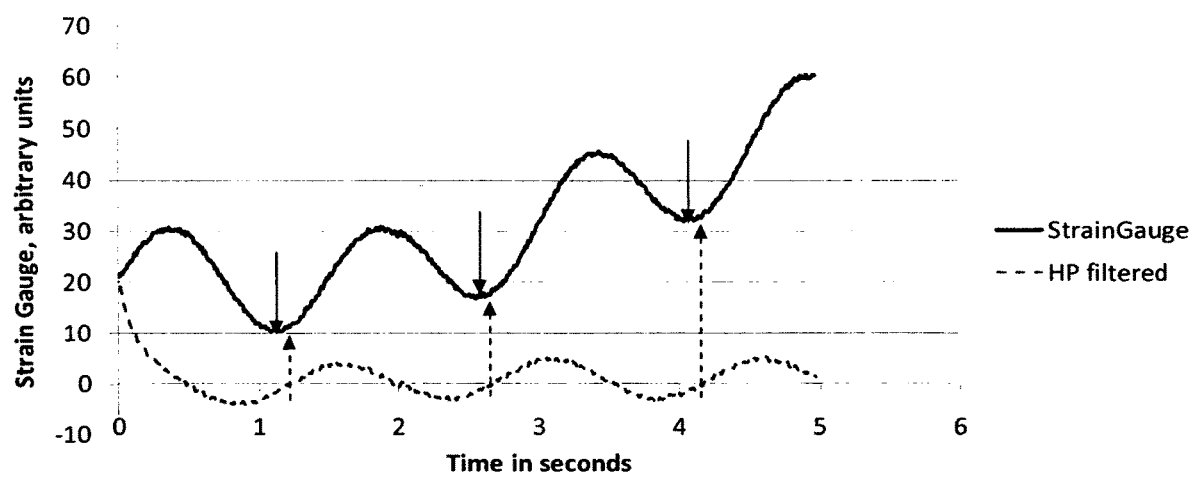
FIG. 5 is a measured and respective filtered strain gauge signal.

As the patient inhales or a ventilator delivers a breath to the patient, the belt-like structure expands and the strain-gauge measures this expansion. The sensor signal is converted to digital format, typically at 50 to 100 samples per second, and may be analyzed digitally. Analysis may include a simple low-pass filter and subsequent determination of minimal force. Alternatively, analysis may be done as in FIG. 5, illustrating the analysis of a strain gauge signal to find the EIT reference vector in presence of significant signal drift. Arbitrary units of a strain gauge (solid line) and its derivative (for example high-pass filter at RC=0.1 sec, dotted line) are plotted during breathing while the lung volume is being continuously changed. The local minimum of the strain gauge (solid arrows) is around 0.1 second before every zero crossing of its high-pass filtered derivative (dotted arrows).

The sensor data, typically from a strain gauge, is first filtered by a low-pass filter with a cut-off frequency of 20 Hz. Thereafter, a high-pass filter is employed with a cut-off frequency of 0.1 Hz. If the so filtered curve crosses the zero-line going from low force to high force (dotted arrows), the chest is starting to expand and thus this point is taken as "start of inhalation". The EIT data vector measured at this point in time, or a predefined lead time earlier, typically one time constant of the high-pass filter earlier, is taken as the reference vector for subsequent differential EIT imaging. This procedure will introduce a slight delay in the image sequence which, however, is clinically irrelevant.

Alternatively, the breathing activity is measured by a second acceleration sensor (e.g. replacing above mentioned strain gauge sensor). Since the chest is moving with every breath, the second acceleration sensor can sense this movement and turn it into a signal that can be used to indicate the onset of inhalation and to determine the reference vector as described above.

Further alternatively, the same acceleration sensor measures both, the breathing activity and the direction (i.e. orientation) of the gravity vector relative to the observation plane. For this purpose a 3D acceleration sensor may be used.

In another embodiment, the temporal data sensor is an electrical activity sensor, for example a sensor as used in electrocardiography (ECG), i.e. an electro-cardiography sensor. Such a sensor can be used to create reference images related to the onset of the heart contraction thereby creating a "heart reference data vector". Thereafter, the "heart reference data vector" is subtracted from each EIT data, making visible impedance changes that are caused by heart activity.

In another embodiment, the temporal data sensor is an acoustic activity sensor or microphone, for example a sensor as used in phonocardiography (PCG), i.e. a phonocardiography sensor. Such a sensor can be used to create reference images related to the onset of the heart contraction thereby creating a "heart reference data vector". Thereafter, the "heart reference data vector" is subtracted from each EIT data, making visible impedance changes that are caused by heart activity.

In another embodiment, at least two temporal data sensors are combined with a spatial data sensor. For example, an electrical or acoustic activity sensor, e.g. a sensor as used in electrocardiography or phonocardiography, respectively, and a dilation sensor, e.g. a strain gauge sensor, are combined with a 3-D acceleration sensor (spatial data sensor). This allows to measure orientation of the observation plane with respect to the gravity and at the same time dilation of the electrode belt due to breathing and electrical activity due to cardiac activity.

DESCRIPTION OF USE OF THE INVENTION

The present invention can be used to enhance the image quality of EIT devices in stand-alone monitors and in mechanical ventilators and anaesthesia machines. Such improvement can be done by either creating the enhanced images or by plotting the gravity vector directly on the image, or automatically rotating the image with respect to the gravitational vector thereby providing orientation to the user. A particular use of such improved EIT images is to initiate specific therapies such as recruitment manoeuvres, physiotherapy, or changes in posture and to measure the effectiveness of the therapeutic interventions.

A typical application of the sensor device for EIT imaging, the EIT imaging instrument and EIT imaging method according to present invention is in mechanically ventilated intensive care patients. About 15% of these patients suffer from acute lung injury and more than 30% of these die. It is estimated that about half of these patients could be saved by adequate treatment. Such treatment involves lung recruitment to effectively minimize zones 2 and 3. However, lung recruitment manoeuvres entail risks. Clinicians therefore often use lung recruitments only when lung damage has already become obvious. Unfortunately, this is often too late. With the disclosed invention, a care provider would have the means to judge the need and the success of lung recruitment manoeuvres early in disease, save lives, and reduce cost of care.

In another use, the context sensitive EIT can be used to optimize the body position of a patient with respect to lung function.

EXAMPLE

Below is depicted an example for reconstructing an EIT image by using the finite element method and adjusting raw EIT data with respect to position and orientation of the patient according to present invention.

The reconstruction problem is solved using the finite-element method (FEM). The FEM uses a mesh of triangular elements, defined by nodes, to discretize the space or surface of interest. Then the physics of the problem is applied to the mesh and the problem is solved using given boundary conditions.

Doing this for EIT, one gets $$Y(\sigma)*V=C,$$

where Y is the conductance matrix, depending on the conductivity $\sigma$, V is a set of voltage distribution and C is a set of applied currents.

Given that one can only measure the voltage at the medium's boundary at given locations (i.e. at the electrodes) the operator D is introduced. It returns a vector v of voltage measurements corresponding to a given system and scanning pattern, $$v=D(V)=D(Y^{-1}*C).$$

The above equation is then linearized with respect to $\sigma$ using Taylor expansion, $$\Delta v = S \Delta \sigma,$$

where S is the sensitivity matrix $$\left.\frac{\delta v}{\delta \sigma}\right|_{\sigma_0},$$

$\Delta \sigma$ is $\sigma - \sigma_0$,
and $\Delta v$ is $v - v_0$.

For a given change in the measurements $\Delta v$, we thus obtain a change in conductivity $\Delta \sigma$. In the image reconstruction process, the idea is to find the change in conductivity $\Delta \sigma$ from a given change in the measurements $\Delta v$.

To compute $\Delta \sigma$ one has to invert the matrix S. This operation is in general non-trivial and cannot be performed using the classical inverse of a matrix. This category of problem is known in the literature as inverse ill-posed problems. This means that the problem has more unknowns than equations. A way to calculate solutions, despite the ill-posed nature, is to use a regularization technique which implies that some assumptions are made about the medium of interest. The idea in EIT is essentially to find a least-square solution $\Delta \sigma$ of the problem ($\|S\Delta\sigma-\Delta v\|^2$). Since the problem is ill-posed, a regularization term is added yielding the following cost function (see, for example, Adler A, Guardo R, Electrical impedance tomography: regularised imaging and contrast detection, IEEE Trans Med Imaging, 1996, 15 170-9):

$$\Phi = \frac{1}{2}\|S\Delta\sigma - \Delta v\|^2 + \frac{\lambda}{2}\|F\Delta\sigma\|, \tag{I}$$

where $\lambda$ is the weighting term of the regularization term and F is a spatial high-pass filter matrix.

One can note that the use of the Euclidian norm (squared) is not mandatory; another norm can also be used.

In the art (Adler and Guardo, 1996), $F_{freq}$ can be modeled as a high-pass Gaussian spatial filter of the form:

$$F_{freq}(u, h) = 1 - e^{-\omega_0^2(u^2+h^2)},$$

where $\omega_0$ is the cutoff frequency, and u, h variables are the ordinate, abscissa directions in spatial frequency space, respectively (FIG. 4). The application of this filter results in an image with filtered high spatial frequencies, i.e. a smoother image. It is possible to extend the same idea in order to filter more or less the high frequencies in a particular direction:

$$F_{freq}(u, h) = 1 - e^{-(\omega_u^2 u^2 + \omega_h^2 h^2)},$$

where u'=u cos($\beta$)-h sin($\beta$) and h'=u sin($\beta$)+h cos($\beta$) are the axis direction rotated by an angle $\beta$ (see FIG. 4) around $(u_0, h_0)=(0,0)$. The new cutoff frequencies are $\omega_{u'}$ and $\omega_{h'}$ linked to the u' and h' axis respectively.

Figure 6:
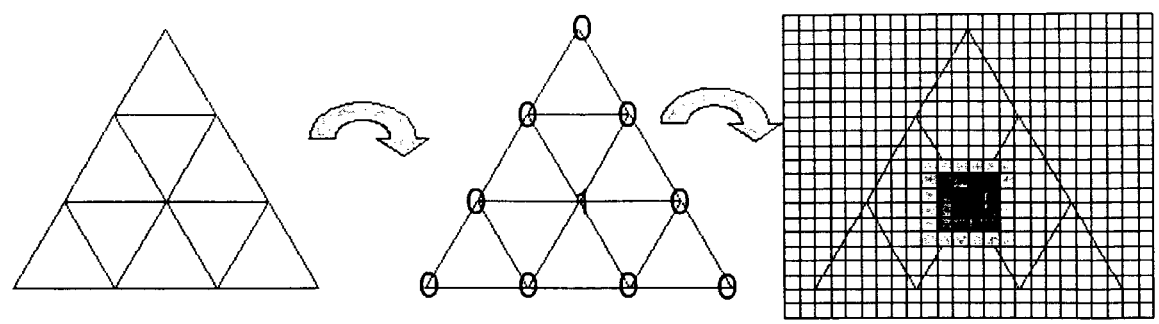
FIG. 6 is a scheme of formation of a pixelized impulse image for one single node of a mesh.

The way to calculate F is given in the following paragraph. First of all it is important to note that F as given in equation (I) is the filter for the finite-element mesh space, so that in order to calculate F the following workflow is used:

FIG. 6 depicts schematically the process used to form the pixelized impulse image for one single node of a mesh. For each mesh node, an impulse image is generated. In other words, for each node, one creates a new mesh where all the node values are set to zero except for the considered node, which is set to one. Then, the meshes obtained are pixilized using a sufficiently fine grid; during this process the impulse images of the meshes are linearly interpolated on their corresponding pixel grids between nodes.

Figure 7:
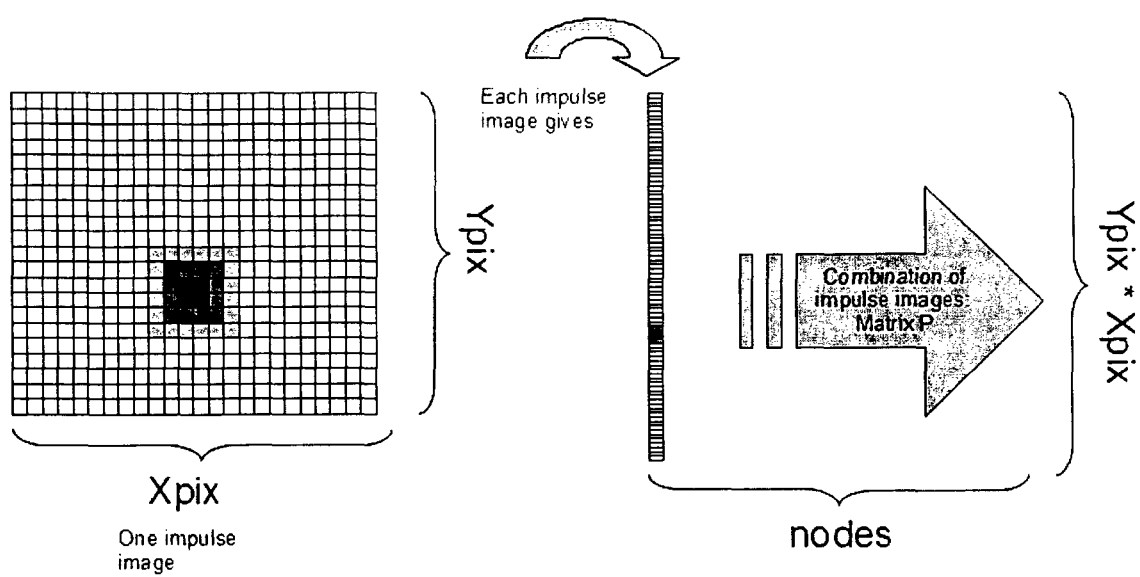
FIG. 7 is a scheme of formation of matrix P.

FIG. 7 depicts the formation of the matrix P. Each image is transformed into a column vector, and all image column vectors are then appended to form a matrix P. This matrix P will be used later on.

Figure 8:
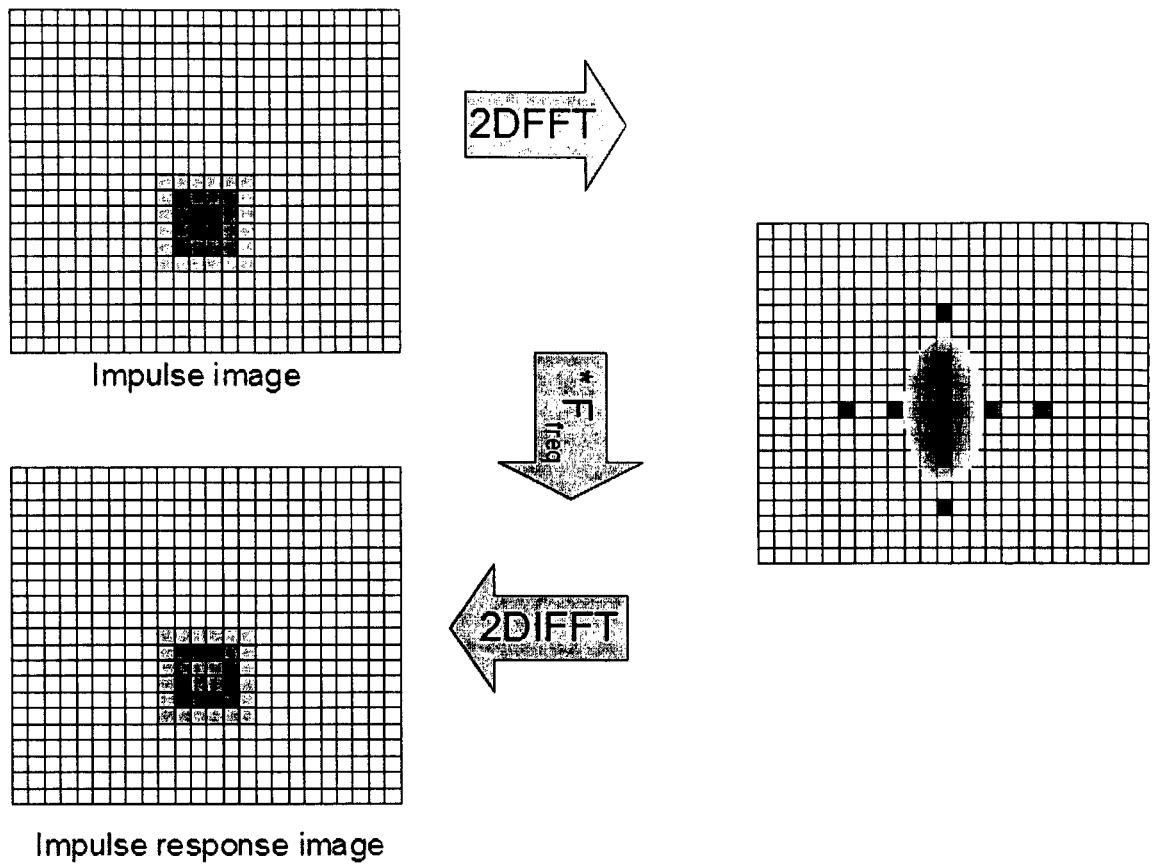
FIG. 8 is a scheme of a filtering process in a spatial frequency domain.

FIG. 8 depicts the filtering process in the spatial frequency domain. At this stage, one also applies a 2D-FFT (two-dimensional Fast Fourier Transform) on the impulse images to go into the spatial frequency domain. The filter $F_{freq}$ is applied and a 2D-IFFT (two-dimensional Inverse Fast Fourier Transform) is performed to go back into the spatial domain. One thus obtains a set of impulse response images.

Figure 9:
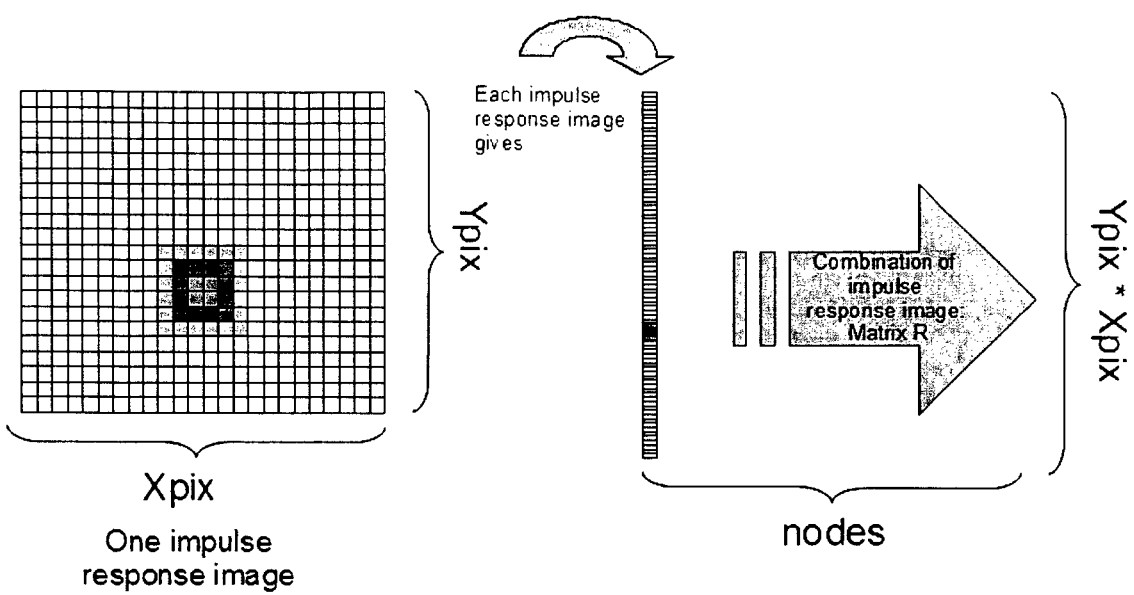
FIG. 9 is a scheme of formation of matrix R.

FIG. 9 depicts the formation of matrix R. Each impulse response image is transformed into a column vector, and all image column vectors are appended to form a matrix R.

The spatial-domain filter matrix F is obtained from the following expression:

$$PF=R.$$

One uses the pseudo-inverse to extract the matrix F:

$$F=[P^TP]^{-1}P^TR.$$

The ratio $$\frac{\omega_{u'}}{\omega_{h'}} = c*\gamma(\alpha) + d$$

(for example, $\gamma(\alpha)=\sin(\alpha)$, $d=c=1$) is one of the main filter parameter and is in direct relationship with the angle $\alpha$.

The invention proposes a sine function for the gamma function but it is understood that any other function could be used. For example, $\gamma(\alpha)=\alpha/90$, $d=1$, $c=0$, where $\alpha$ is between 0 and 90 degrees, could be used. The gamma function could also be a mathematical model that represents the physiological zones (1 to 3) expression described above. The same notice is also valid for the F function, because other spatial filtering shapes could be used, for example a rectangle or an ellipse.

While the invention has been described above with reference to specific embodiments and examples thereof, it is apparent that many changes, modifications, and variations can be made without departing from their inventive concept disclosed herein. Accordingly, it is intended to embrace all such changes, modifications and variations that fall within the spirit and broad scope of the appended claims.

The invention claimed is:

1. An electrical impedance tomography (EIT) imaging device, comprising:
   an electrode array comprising a plurality of electrodes for measuring an impedance distribution for investigating lung ventilation and perfusion, the plurality of electrodes of the electrode array arranged in or on a belt structure defining an observation plane;
   a first sensor mechanically coupled to the electrode array of the EIT imaging device for determining a spatial orientation of the observation plane with respect to a gravity vector, wherein the EIT imaging instrument is adapted for determining the spatial orientation of the observation plane substantially simultaneously with the measurement of the impedance distribution; and
   a computing device for presenting electrical impedance tomography images of the observation plane with respect to the gravity vector, the computing device configured for presenting zones with open and well aerated alveoli, zones with unstable alveoli in which their opening and closing occurs during a respiratory cycle and zones with collapsed alveoli, and the computing device configured for presenting a variation in a degree or level of zone expression within lungs of a patient with respect to the gravity vector after changing a body position of the patient or after a treatment.

2. The EIT imaging device of claim 1, wherein the computing device is configured for adjusting impedance data based on at least one of dilation data, acoustic activity data or electrical activity data.

3. The EIT imaging device of claim 1, further comprising at least one second sensor connectable to the EIT imaging device for gathering information on at least one of electrical activity, acoustic activity or dilation.

4. The EIT imaging device of claim 3, wherein the computing device is configured for automatically rotating the electrical impedance tomography images with respect to the gravitational vector.

5. The EIT imaging device of claim 1, wherein the at least one first sensor for determining the spatial orientation comprises a three-dimensional acceleration sensor.

6. The EIT imaging device of claim 1 comprising at least one second sensor for gathering information on electrical activity coupled to the electrode array.

7. The EIT imaging device of claim 6, wherein the at least one second sensor for gathering information on electrical activity comprises an electro-cardiography sensor.

8. The EIT imaging device of claim 1 further comprising at least one second sensor for gathering information on acoustic activity coupled to the electrode array.

9. The EIT imaging device of claim 8 wherein the at least one second sensor for gathering information on acoustic activity comprises a microphone or a phonocardiography sensor.

10. The EIT imaging device of claim 1 further comprising at least one second sensor for gathering information on changes in dilation of the electrode array integrated in or attached to the electrode array.

11. The EIT imaging device of claim 10 wherein the at least one second sensor for gathering information on changes in the dilation comprises a strain gauge.

12. An electrical impedance tomography (EIT) imaging method for measuring an impedance distribution and adjusting a measured impedance distribution, comprising:
    measuring impedance distribution for investigating lung ventilation and perfusion with an impedance distribution measuring device comprising an electrode array comprising a plurality of electrodes defining an observation plane,
    determining a spatial orientation of the observation plane with respect to a gravity vector approximately simultaneously with the measuring of the impedance distribution,
    presenting electrical impedance tomography images of the observation plane with respect to the gravity vector, and
    presenting zones with open and well aerated alveoli, zones with unstable alveoli in which their opening and closing occurs during the respiratory cycle and zones with collapsed alveoli, and
    presenting a variation in a degree or level of zone expression within lungs of a patient with respect to the gravity vector after changing the body position of the patient and/or after a treatment.

13. The EIT imaging method of claim 12, further comprising determining a corresponding spatial orientation of the patient by measuring the spatial orientation of the electrode array of the impedance distribution measuring device.

14. The EIT imaging method of claim 12, further comprising determining a corresponding spatial orientation of the patient while measuring the impedance distribution.

15. The EIT imaging method of claim 12, further comprising determining a corresponding spatial orientation of the patient approximately simultaneously with the measurement of the impedance distribution.

16. The EIT imaging method of claim 12, further comprising measuring values of the impedance distribution and determining a corresponding spatial orientation of the patient within at least one of 1 second, 500 milliseconds, 100 milliseconds, and 10 milliseconds of measuring values of the impedance distribution.

17. The EIT imaging method of claim 12, further comprising adjusting the measured impedance distribution according to at least one of:
    electrical activity,
    acoustic activity, or
    dilation of an observation area.

18. The EIT imaging method of claim 12, wherein the plurality of electrodes is arranged in or on a belt structure.

* * * * *